US010980951B1

(12) United States Patent
Walters

(10) Patent No.: US 10,980,951 B1
(45) Date of Patent: Apr. 20, 2021

(54) NEBULIZER

(71) Applicant: Donald Lee Walters, La Serenta, CA (US)

(72) Inventor: Donald Lee Walters, La Serenta, CA (US)

( * ) Notice: Subject to any disclaimer, the term of this patent is extended or adjusted under 35 U.S.C. 154(b) by 0 days.

(21) Appl. No.: 17/247,685

(22) Filed: Dec. 21, 2020

(51) Int. Cl.
*A61M 11/00* (2006.01)
*A61M 15/08* (2006.01)

(52) U.S. Cl.
CPC .......... *A61M 11/005* (2013.01); *A61M 15/08* (2013.01); *A61M 2205/0294* (2013.01); *A61M 2205/3553* (2013.01); *A61M 2205/52* (2013.01)

(58) Field of Classification Search
CPC ........ A24B 15/167; A24F 40/05; A24F 40/10; A24F 40/40; A24F 40/42; A24F 40/46; A24F 40/48; A24F 47/002; A24F 47/008; A61K 31/05; A61K 31/352; A61K 31/465; A61K 9/0073; A61K 9/127; A61M 11/001; A61M 11/002; A61M 11/005; A61M 11/04; A61M 11/041; A61M 11/042; A61M 15/001; A61M 15/0021; A61M 15/0023; A61M 15/0085; A61M 15/009; A61M 15/06; A61M 15/085; A61M 16/0003; A61M 16/0672; A61M 16/0808; A61M 16/0816; A61M 16/14; A61M 2016/0015; A61M 2016/0021; A61M 2202/04; A61M 2202/0468; A61M 2205/0294; A61M 2205/10; A61M 2205/103; A61M 2205/106; A61M 2205/3334; A61M 2205/3633; A61M 2205/8206; B05B 15/58; B05B 17/0615; B05B 17/0638; B05B 7/0012; B05B 7/16; B65D 83/0011
See application file for complete search history.

(56) References Cited

U.S. PATENT DOCUMENTS

| | | | |
|---|---|---|---|
| 5,152,456 A | 10/1992 | Ross et al. | |
| 8,056,557 B2 * | 11/2011 | Lieberman | ........... A61M 11/005 128/200.16 |
| 9,038,625 B2 * | 5/2015 | Hu | ........ A61M 11/005 128/200.16 |
| 10,888,117 B2 * | 1/2021 | Danek | ................... A61M 11/005 |
| 2002/0129812 A1 | 9/2002 | Litherland et al. | |
| 2003/0037788 A1 | 2/2003 | Gallem et al. | |
| 2003/0062038 A1 | 4/2003 | Tanaka et al. | |
| 2019/0366016 A1 * | 12/2019 | Leonard | ................ A61M 16/14 |
| 2020/0060349 A1 * | 2/2020 | Danek | ................ A61M 15/0021 |
| 2020/0230329 A1 * | 7/2020 | Danek | ................... A61M 11/042 |

OTHER PUBLICATIONS

U.S. Appl. No. 16/443,173, filed Jun. 17, 2019, Walters, Donald.

* cited by examiner

*Primary Examiner* — Annette Dixon
(74) *Attorney, Agent, or Firm* — Carson Patents®; Gregory D Carson

(57) ABSTRACT

This invention relates to nebulizers, which are machines that change a liquid form to a mist consisting of micron sized droplets. More specifically the invention relates to liquid medicament nebulizers, for example for delivering a mist of medicament to eyes, nasal passages, and lungs. A housing has a form which rolls to house first and second reservoirs, an expansion chamber, and a vibration element. The housing has a center of mass which urges the nebulizer to roll toward a storage position where the liquid drains from the first reservoir through the drain passage to the second reservoir.

20 Claims, 4 Drawing Sheets

NEBULIZER

FIELD OF THE INVENTION

This invention relates to nebulizers, which are machines that change a liquid form to a mist consisting of micron size droplets. More specifically the invention relates to liquid medicament nebulizers, for example for delivering a mist of medicament to eyes, nasal passages, and lungs. More specifically the invention relates to intranasal insulin therapy.

BACKGROUND

Research has proven that there is a need and utility to nebulizing various medicaments using a mist delivery method. The various medicaments proven useful include, but are not limited to, a wide variety of solutions and suspensions including insulin, peptides, proteins, and inert vaccines.

In the past a small hand-held manual spritzer bottle has been used to squirt a mist of medicament directly into the nose, to be absorbed by the nasal mucosa. This device and method has limited efficacy because of a wide range of droplet size produced and imprecise control of the amount of medicament delivered by a squirt.

Nebulizers such as disclosed in publication US-A-20030062038 (Tanaka) achieve a more precise range of droplet size and dosage control ejecting the medicament through precisely sized apertures. However, there are difficulties with filling and storage of the medicament in these nebulizers.

SUMMARY OF THE INVENTION

According to one aspect of the present invention, there is a nebulizer for nebulizing a liquid into a mist comprising the following: a first reservoir and a second reservoir having a first drain passage for the liquid to the first reservoir; an expansion chamber having a first side adjacent to the first reservoir and an exit to the exterior of said nebulizer, the expansion chamber being configured to channel the mist nebulized from the liquid out of the nebulizer through the exit; a vibration element disposed between said opening of said expansion chamber and said first reservoir, the vibration element having a porous mesh through which the liquid in said first reservoir is nebulized into the mist on activation of the vibration element. The nebulizer has a shape and weight distribution to rest in a stable storage position and roll toward a stable storage position from any other position. In a stable storage position, the liquid drains from the first reservoir through the first drain passage to the second reservoir. So there is no undesirable seepage of the liquid through the porous mesh out of the nebulizer in the storage position. The nebulizer may have a center of mass offset from an axis of rotation to urge the nebulizer to roll toward the storage position.

Preferably, the nebulizer comprises the liquid. Preferably, the nebulizer comprises a third reservoir having a second drain passage for said liquid to the second reservoir. In the stable storage position, the liquid drains from the second reservoir through the second drain passage to the third reservoir in the storage position. The liquid may be contained in the second reservoir and/or the third reservoir.

The second reservoir is preferably, disposed to drain the liquid into the first reservoir to contact the mesh when the nebulizer is in a mist generating position. The third reservoir is preferably, disposed to share drainage of the liquid with the second reservoir. So the vibration element can drive the liquid in the first reservoir as a mist of droplets is made as the liquid is driven through the pores into the expansion chamber.

The second reservoir may be offset from the mesh. Preferably, the second reservoir is offset in a direction parallel to the planar vibration element so that the liquid may drain down into the first reservoir when the nebulizer is in the mist generation position.

The nebulizer may have a tubular housing 199 configured to house the first reservoir, the second reservoir, the first drain passage, and the vibrating element. The exit of the expansion chamber may be through an external wall of the housing 199. Preferably, the exit faces upward with the nebulizer in the storage position. In the preferred storage position, any remaining liquid in the first reservoir will drip down away from the mesh and any liquid in the expansion chamber will drain down from the mesh and into the first reservoir, wherein any liquid will then continue to drip down away from the first reservoir and into the second and the third reservoir. To further this objective, preferably, the vibration element is intermediate the exit and the first reservoir. The vibration element may be intermediate the exit and the passage.

The volume of the second reservoir may exceed the volume of the first reservoir. Preferably, the volume of the third reservoir is equal to or exceeds the volume of the second reservoir, so that all the liquid may drain from the first reservoir into the second reservoir to prevent seepage in the storage position and so that a convenient amount of liquid may be continuously drained into the first reservoir from the second reservoir while the nebulizer is in the mist generation position and generating mist.

The mesh may lie in a first plane of the vibration element. Preferably, the mesh lies in a first plane of the vibration element.

In a further variant, the vibration element comprises an ultrasonic piezoelectric ceramic transducer configured to emit ultrasound and comprising a piezoelectric unit configured to vibrate in response to the ultrasound. Preferably, the piezoelectric transducer is configured to vibrate the porous mesh to nebulize the liquid when in the first reservoir.

In yet a further variant, the ultrasonic piezoelectric ceramic transducer may be flat and comprises a solid outer ridge and a central mesh surrounded by the solid outer ridge. The central mesh may have perforations of a desired size to enable passage of droplets of the mist under the desired size. The ultrasonic piezoelectric transducer may be configured for driving the mist particles from the first reservoir to the expansion chamber.

In a variant, vibration of the piezoelectric unit may be configured to generate a mist of insulin having droplets of diameter of 11 micrometers. The perforations of the mesh have a diameter of 12 micrometers.

In another variant, the ultrasonic piezoelectric ceramic transducer operates in pulses, turning on and off a plurality of times during an operation thereof.

In yet another variant, the ultrasonic piezoelectric ceramic transducer is configured to pulse between 200,000 and 400,000 times per minute.

In a further variant, the nebulizer comprises a timer configured for timing an operation of the vibration element and for causing the vibration element to cease vibrating after a predetermined time has passed from a start of the vibrating.

In yet a further variant, the nebulizer comprises a pause button, configured to be pressed by the patient while the vibration element vibrates to pause the operation of the vibration element and pause a timing of the timer, such that when the patient presses the pause button again, the vibration element resumes vibrating and the timer resumes timing from a time point at which the timer had stopped.

The center of mass of the housing may be located on a line which passes through the second reservoir and is parallel to the first plane in which the vibration element is situated. Thus the center of mass is offset from the vibration element to provide a moment which urges the housing to roll to the storage position. Preferably, the second reservoir has a floor of material of the housing axially displaced from the second reservoir and radially displaced from the first reservoir. The center of mass of the floor of material may be offset from the axis of the tubular housing to urge the nebulizer to roll to the stable storage position.

The housing may have a first entryway to put the liquid into the second reservoir and allow the liquid out of the second reservoir.

The shape of the nebulizer may be configured to roll on a flat surface. The housing may have an axis of rolling, around which the expansion chamber, vibration element, first reservoir, passage, and second reservoir rotate when the housing rolls.

Preferably, the mesh is planar and parallel to the axis of rolling. Thus, the expansion chamber may extend straight to an exterior wall of the housing where it exits.

Preferably, the expansion chamber, vibration element, and first reservoir are located on a same side of the axis of rolling, so that the center of mass may be concentrated on the opposite side to make an effective turning moment to urge the nebulizer to the storage position.

The housing may comprise an edge on an opposite side of the axis of rolling as the expansion chamber, the edge configured to stabilize the nebulizer in the stable position against rolling. The storage position is thereby a robust and reliable position when the nebulizer is stored on a surface on which the edge rests.

Preferably, the edge is aligned parallel to a rollable direction of the housing, such that the nebulizer may be in a stable position over an angular range which prevents rocking back and forth past the stable position. Preferably, the storage position is in a stable position against rolling.

The storage position is in a stable position against rolling wherein Preferably, the first and second reservoirs, the first drain passage, the expansion chamber, and the vibration element are disposed toward where the nebulizer is openable and closable to put the liquid in the nebulizer. The housing may comprise a tubular portion configured to roll on a flat surface. Preferably, the first and second reservoirs, the passage, the expansion chamber, and the vibration element are disposed in the tubular portion. The second reservoir may be offset from the mesh in the direction of an axis of rolling of the tubular portion toward where the housing is openable and closable to put liquid.

In the nebulizer, Preferably, in the tubular portion, there may be a cavity offset from the mesh in the direction of the axis of rolling. The cavity may be an electronics bay 155 and/or configured to hold a battery to provide power to the vibration element and motherboard.

There may be a conduit through the housing from the second reservoir to the cavity, the conduit configured for a wire to carry a signal from a sensor in the second reservoir to a circuit in the cavity.

In a variant, the nebulizer comprises a non-volatile memory unit, Preferably, in the cavity configured to store data, and a processing unit configured to process the data and to control an operation of the nebulizer according to operation instructions comprised in the data.

In yet another variant, the nebulizer comprises a sensor data intake unit configured to receive first data collected by one or more sensors associated with the nebulizer and indicative of biological parameters of the patient and to transfer the first data to the non-volatile memory unit for storage.

In a further variant, the non-volatile memory unit is removable, Preferably, from the cavity, and configured to be received by a computing unit in communication with remote database for data transfer between the non-volatile memory unit and the remote database.

In yet a further variant, the nebulizer comprises a communication unit configured to communicate with a computing unit in communication with remote database, the communication unit being configured for data transfer between the non-volatile memory unit and the remote server via the computing unit.

Preferably, the nebulizer comprises a convex base on a longitudinal end of the nebulizer distal from the second reservoir. Preferably, the convex base is on a longitudinal end of the tubular portion distal from the second reservoir, such that the tubular portion is unstable when stood on the convex base end thereby encourages a user to place the housing prone on a surface on which it may roll to the stable position.

Preferably, the tubular portion is cylindrical. However, the tubular portion may have a polygonal cross section providing flat facets on the outer surface, or the tubular portion may have an oval cross section. The moment (i.e. torque) caused by the center of mass of the housing being offset from the axis of rotation may overcome any resistance to roll by cross section on a surface. So the torque will roll the tubular portion and overcome rolling resistance of the facets or ovalness.

Preferably, the nebulizer comprises a nose inhalation device having an inlet joined to the exit of the expansion chamber and configured to receive the mist from the expansion chamber. Preferably, the nose inhalation device is joined to the exit in the housing.

The nebulizer of the present invention is configured to administer medicaments by only requiring a patient to breathe the mist naturally through the nose. The weight of the droplet determines where it will go. No special breathing technique is required. For medicaments with a specific gravity similar to water, such as insulin, nebulized droplets less than 9 micrometers in diameter will be breathed into lungs; droplets in a range of 10 micrometers to 17 micrometers are breathed into the nasal passage where the medicament is absorbed; and droplets over 17 micrometers are breathed direct to the throat and the medicament is swallowed.

Preferably, the nose inhalation device has a curved lip which provides an unstable rest on a rolling surface which urges the nebulizer to roll toward a storage position when resting on the lip of the nose inhalation device and preferably, also when resting on the housing In another variant, the nose inhalation device comprises a flat portion surrounding the inlet of the nose inhalation device and having a plurality of air holes configured for allowing passage of air therethrough.

In an alternate embodiment, the mesh comprises pores to generate mist which the liquid may seep through which are 10 to 17 micrometers in diameter or which have a widest dimension of 11 to 17 microns. Preferably, the perforations are between 10 micrometers and 13 micrometers at the widest part of the perforation.

Some embodiments of the present invention are directed at a nebulizer that produces a metered dose of a medicament as a mist having droplets of diameter of 11 µm. This is produced by a piezoelectric nanoparticle transducer. If a larger nanoparticle is required, the nebulizer of the present invention would require a different transducer element.

In a variant, the expansion chamber is removable from a remainder of the housing.

In another variant, the vibration element is accessible from an outside of the housing when the expansion chamber has been removed.

In yet another variant, the vibration element is removable from the housing when the expansion chamber has been removed.

In a further variant, the nebulizer comprises a plurality of vibration elements, each vibration element configured for generating a respective mist having droplets of a respective size, such that any one of the plurality of vibration elements is placed in the housing at one time to generate the respective mist.

In yet a further variant, the expansion tube is removable from the expansion chamber.

In a variant, the nebulizer comprises a plurality of expansion tubes having respective lengths, each of the expansion tubes being configured for being removably joined to the first front side of the expansion chamber.

According to another aspect of the present invention, there is a nebulizer, comprising a first reservoir, an expansion chamber, a vibration element, an expansion tube, a nose inhalation device, and a housing. The first reservoir is configured to contain a liquid medicament. The expansion chamber has a first rear side adjacent to the first reservoir and a first front side opening to an outside environment, the expansion chamber being configured to lead a mist generated from the liquid medicament out of the nebulizer device. The vibration element is disposed between the first rear side of the expansion chamber and the first reservoir, the vibration element having a second rear side facing the first reservoir and in contact with the medicament in the first reservoir and being configured to vibrate upon an instruction from a user to turn the liquid medicament into the mist having droplets of a desired size, the vibration element preventing passage of the liquid medicament from the first reservoir to the expansion chamber and allowing passage of the mist from the first reservoir to the expansion chamber. The expansion tube has a first open end and a second open end, the first end being joined to the first front side of the expansion chamber, the expansion tube being configured for directing the mist from the expansion chamber to the second open end. The nose inhalation device has an inlet joined to the second open end of the expansion tube and configured to receive the mist from the expansion tube, the nose inhalation device being configured for surrounding a nose of the user, such that the mist is delivered to the user's nasal cavity through normal breathing of the user. The housing is configured to house the first reservoir, the expansion chamber, and the vibration element.

According to another aspect of the invention, there is a method of repositioning a nebulizer as disclosed in the storage position from a position where the second reservoir is disposed to drain the liquid into the first reservoir to contact the mesh, including laying the housing on a flat surface and allowing the nebulizer to roll toward the stable position.

The nebulizer, may have an axis of rolling around which the expansion chamber, vibration element, first reservoir, passage, and second reservoir rotate when the nebulizer rolls. Preferably, the axis of rolling is a tubular axis of the housing. The nebulizer may comprise an edge on an opposite side of the axis of rolling as the expansion chamber, the edge configured to stabilize the nebulizer in the stable position against rolling; the method including laying the edge on the flat surface to set the nebulizer in the stable position. Preferably, the edge is an edge of the housing such as an additional straight edge in a radial plane of the tubular axis.

The invention will now be described, by way of example only, with reference to the accompanying drawings in which:

DETAILED DESCRIPTION OF THE INVENTION

Figure 1:
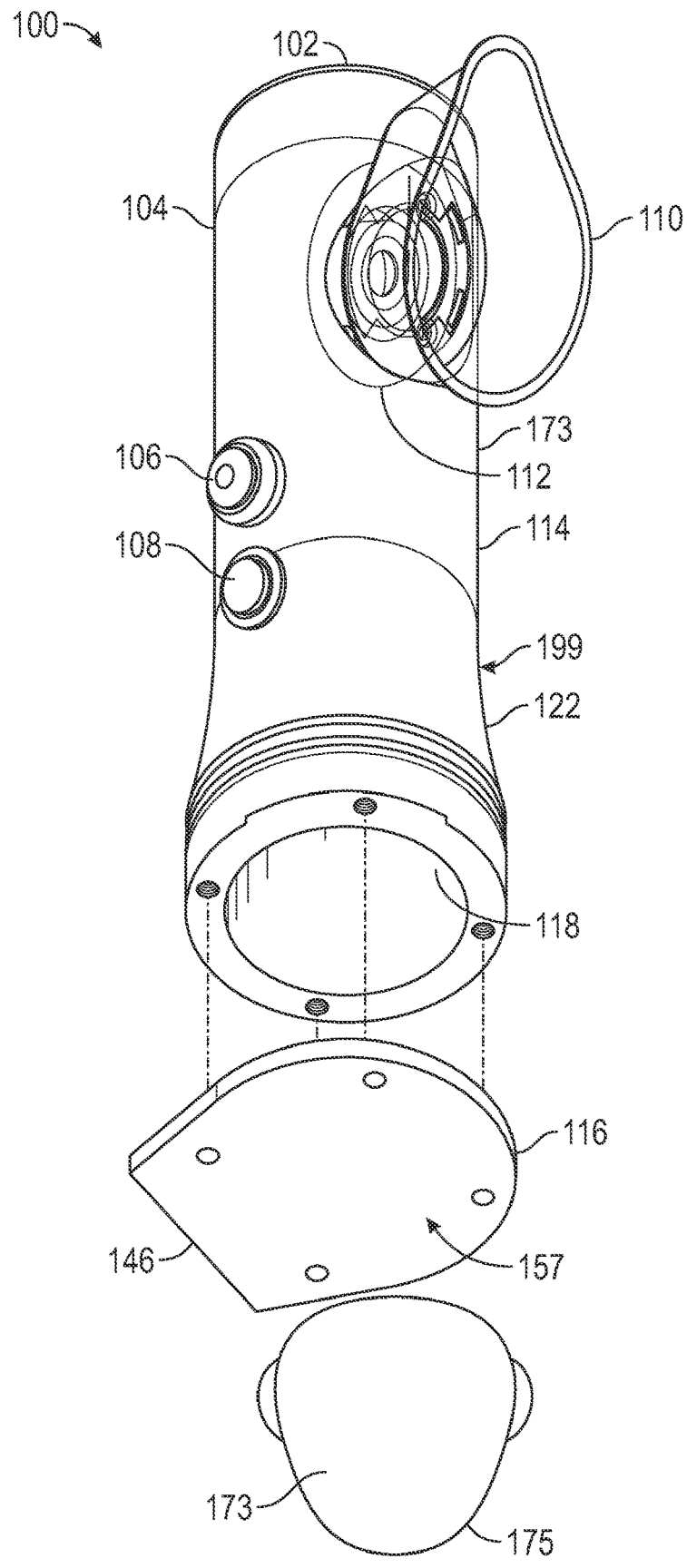
FIG. 1 is a perspective view of the exterior of a nebulizer.

As shown in the figures, the nebulizer 100 comprises the following: a first reservoir 113 and a second reservoir 139 having a first drain passage 161 for a liquid to drain from the first reservoir 113 to/from the second reservoir 139; an expansion chamber 182 having a first side adjacent to the first reservoir 113, the expansion chamber 182 being configured to channel a mist generated from the liquid in the first reservoir 113 out of the nebulizer 100; a vibration element 135 disposed between the first side and the first reservoir 113, the vibration element 135 having a porous mesh 140 through which the liquid when in the first reservoir 113 seeps into the expansion chamber 182; the porous mesh configured to generate the mist upon vibration by the vibration element 135; and a housing 199 having a form which rolls to house the first reservoir 113 and second reservoir 139, the expansion chamber 182, and the vibration element 135, the housing 199 has a center of mass which urges the nebulizer to roll toward a storage position where the liquid drains from the first reservoir 113 through the first drain passage 161 to the second reservoir 139.

When the nebulizer is in the storage position, there is no liquid in the first reservoir 113 and so the liquid cannot seep out of the nebulizer through the pores in the mesh.

Figure 4:
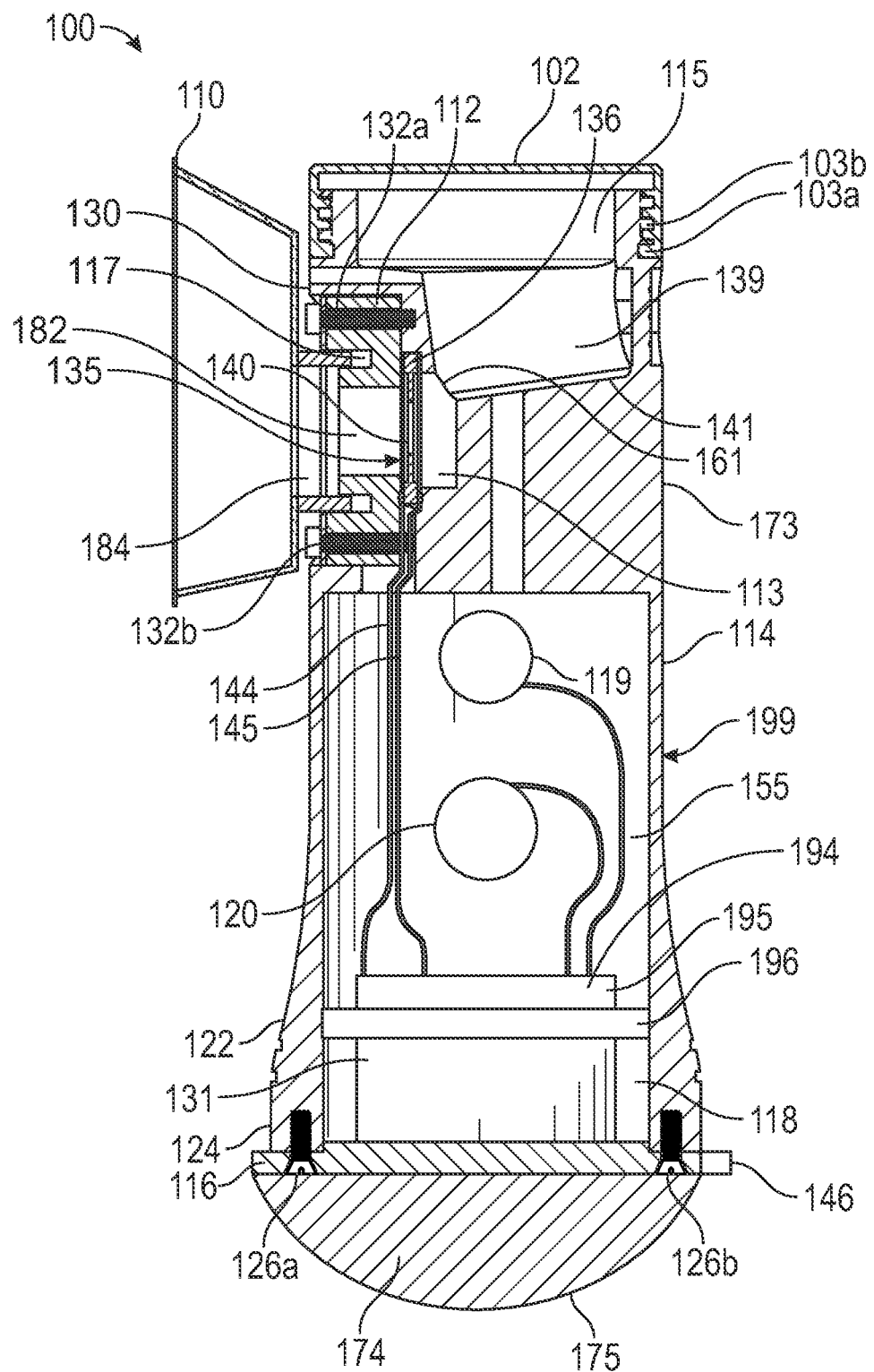
FIG. 4 is a section view of a nebulizer.

Referring now to the drawings, FIG. 1 is a perspective view of the exterior of a nebulizer 100, according to some embodiments of the present invention. FIG. 4 is a cross-sectional side view of the nebulizer 100, according to some embodiments of the present invention.

The nebulizer 100 is configured to contain a medicament in liquid form and generate therefrom a mist having droplets of desired size (diameter). The nebulizer 100 includes a first reservoir 113, an expansion chamber 182, a vibration element 135, an expansion tube 184, a nose inhalation device 110, and a housing 199. In some embodiments of the present invention, the nebulizer 100 is configured to nebulize insulin into a mist and deliver the mist having droplets between 10 µm and 17 µm to the user's nose. The insulin may be, for example, Novolin R, which is available over the counter in pharmacies. In some embodiments of the present invention, the nebulizer 100 is portable and may be used on the move.

The housing 199 contains the reservoirs (first reservoir 113, second reservoir 139, and third reservoir 115), which is configured to store the medicament in liquid form. In some embodiment of the present invention, the housing 199 is made of a rigid material. The rigid material may include, for example Polyoxymethylene, or a variant thereof called DELRIN®. In some embodiments of the present invention, a tapered section 122 of tubular portion 114 of the housing 199 which extends in an axial direction of a cylindrical section 173 of the housing 199. The cylindrical section 173 is proximate a first open end 104 of the housing 199 where there is a first entryway which opens into the third reservoir 115. The tapered section 122 extends toward the opposite second entryway 118 of the housing 199. The tapered section 122 diameter increases as it extends toward the opposite second entryway 118. At the cylindrical rim 124 of the housing 199 at the second entryway 118, the tapered section 122 has a larger diameter and is wider than the cylindrical section 173 of the housing 199. The tapered section 122 tapers upwards towards cylindrical section 173 and the cylindrical rim 124 of housing 199 where the first reservoir 113 is located (i.e. becomes thinner as the height of the tapered section 122 grows toward the first reservoir 113).

When the nebulizer 100 is in a storage position, the housing 199 is substantially prone. For example, as the housing 199 rests substantially prone on a substantially horizontal surface, such as a counter top, sink top, or table top, the tapered section 122 of the housing 199 has a largest diameter at the second end. So when the housing 199 rests on the substantially horizontal surface, the housing 199 slants downward from the second end toward the first open end 104. Consequently, the first reservoir 113 is elevated with respect to the second reservoir 139 by the slant of the housing 199. Since the first reservoir 113 is closer to the tapered section 122 than the second reservoir 139, the slant thus aids drainage of the liquid from the first reservoir 113 into the second reservoir 139. Since the second reservoir 139 is closer to the tapered section 122 than the third reservoir 115, the slant of the housing 199 aids drainage of the liquid from the second reservoir 139 into the third reservoir 115.

When the nebulizer is in the storage position, the liquid is drained out of the first reservoir 113 so that the liquid cannot seep through the porous mesh, which provides a porous wall between the expansion chamber 182 and the first reservoir 113. Therefore, the liquid is not lost due to unwanted seepage through the porous mesh.

The expansion chamber 182 disperses droplets in the mist and opens to the outside of the housing 199 and is separated from the first reservoir 113 via the vibration element 135. In some embodiments of the present invention, a third reservoir 115 and a second reservoir 139 are located above the first reservoir 113. The third reservoir 115 is in fluid communication with the second reservoir 139, while the second reservoir 139 is in fluid communication with the first reservoir 113. The medicament is poured into the third reservoir 115, flows down to the second reservoir 139, and then drains down over the floor 141 of the second reservoir 139 into the first reservoir 113 via the first drain passage 161. The reason for having three reservoirs disposed vertically one above the other is because a single first reservoir 113 in which the medicament contacts the vibration element 135 is too small, as space has to be set aside for the vibration element 135 and the expansion chamber 182 and also to maintain a head of pressure on the liquid in the first reservoir 113.

The vibration element 135 comprises a washer shaped piezo actuator 136 around a planar porous mesh 140. The porous mesh 140 comprises microscopic pores between 10 micrometers and 17 micrometers in diameter or at the widest dimension. The piezo actuator 136 is attached to the porous mesh 140 to vibrate the porous mesh 140 rapidly toward and away from the liquid in the first reservoir 113. The liquid is thereby forced through the pores and driven into the expansion chamber 182 as a fine mist of droplets about 10 micrometers to 17 micrometers in diameter.

Thus, stacking reservoirs vertically allows enough space to store the medicament.

When liquid medicament is in the first reservoir 113, the vibration element 135 vibrates at a desired frequency, and in doing so nebulizes the medicament in the first reservoir 113 into a mist having droplets of a desired size. The droplets are able to traverse the vibration element 135 and are pumped from the first reservoir 113 to the expansion chamber 182, to be released toward the patient. In some embodiments of the present invention, the vibration element 135 is an ultrasonic piezoelectric ceramic transducer. The transducer emits ultrasound, which causes a piezoelectric unit thereof to vibrate at a desired frequency configured to nebulize the liquid medicament. The ultrasonic piezoelectric ceramic transducer not only produces a mist, but also directs the mist into the expansion chamber 182 towards the nose inhalation device 110.

In some embodiments of the present invention, the vibration element 135 is replaceable. This allows the nebulizer 100 to be used to create different mists according to different needs for different medicines and different treatment regimes, each mist having droplets of a respective size.

The vibration element 135 is powered by electrical power provided by a battery (e.g., a 5V battery) located in the electronics bay 155 or via an outer source of electric power connected to the electronics bay 155. The electronics bay 155 is divided into two compartments by a separator 196. The battery 131 is in a second compartment proximate the second entryway 118 of the housing 199. An electronic circuit 195 to take signals from the user via switches and pause button 106, and on/off button 108 to activate the vibration element 135 is in a first compartment proximate the expansion chamber 182.

A first wire 144 and a second wire 145 connect electronically to the vibration element 135 to the electronics bay 155, to transfer the power to the vibration element 135. There is a wire channel between the electronics bay 155 and vibration element 135 traversed by the wires 144 and 145.

The wires 144 and 145 used for ultrasonic transducers are generally not very pliable and are fragile. The wire channel protects the wires 144 and 145, and the angled orientation of the wire channel allows the wires to curve gently before reaching the electronics bay 155.

The expansion tube 184 is a tube having a first end joined to the housing 199 at the exit of the expansion chamber 182 and a second end joined to the nose inhalation device 110. The mist travels from the expansion chamber 182 to the nose inhalation device 110 via the expansion tube. The length of the expansion tube 184 determines the size of the droplets of the mist before the droplets enter the nose inhalation device 110 and the user's nose. The longer the expansion tube 184, the larger the distance to be traversed by the droplets, and therefore, the more time for the droplets of the mist to coalesce (rejoin) and form larger droplets, which is not desired.

In some embodiments of the present invention, the expansion tube 184 is detachable from a tubular or cylindrical wall 112 of expansion chamber 182 and from the nose inhalation device 110. In this manner, differently sized tubes may be used according to the user's needs. In some embodiments of the present invention, a kit is provided, having a single housing 199, at least one nose inhalation device 110, and a plurality of differently size expansion tubes. For a given vibration element 135, which vibrates at a given frequency and produces the droplets having a certain size, each expansion tube 184 enlarges the size of the droplets. In this manner, an appropriate expansion tube 184 can be used to yield mists having droplets of a desired size.

In a variant, a friction groove 117 is cut on the outer side of the cylindrical wall 112 of the expansion chamber 182. The expansion tube 184 of the nose inhalation device 110 is insertable into the friction groove 117 to be joined to the cylindrical wall 112, and removable from the friction groove 117 to be removed from the cylindrical wall 112. In some embodiments, the expansion tube 184 has a friction tapered slip joint on the end facing the friction groove 117. The friction tapered slip joint enhances the ease of insertion of the expansion tube 184 into a friction groove 117 and eases the removal of the expansion tube 184 from the friction groove 117. The removal may be performed for cleaning the expansion tube 184 or replacing one expansion tube 184 with another. In some embodiments of the present invention, the friction groove 117 is also tapered to better hold the friction tapered slip joint.

The nose inhalation device 110 is shaped to surround the user's nose, to facilitate the delivery of the mist to the user's nose. This enables a desired amount of mist to reach the user's nose. In some embodiments of the present invention, a plurality of differently sized nose inhalation devices 110 are compatible with a single housing 199, each nose inhalation device 110 being configured for fitting a respective shape and size of users' faces.

Figure 3:
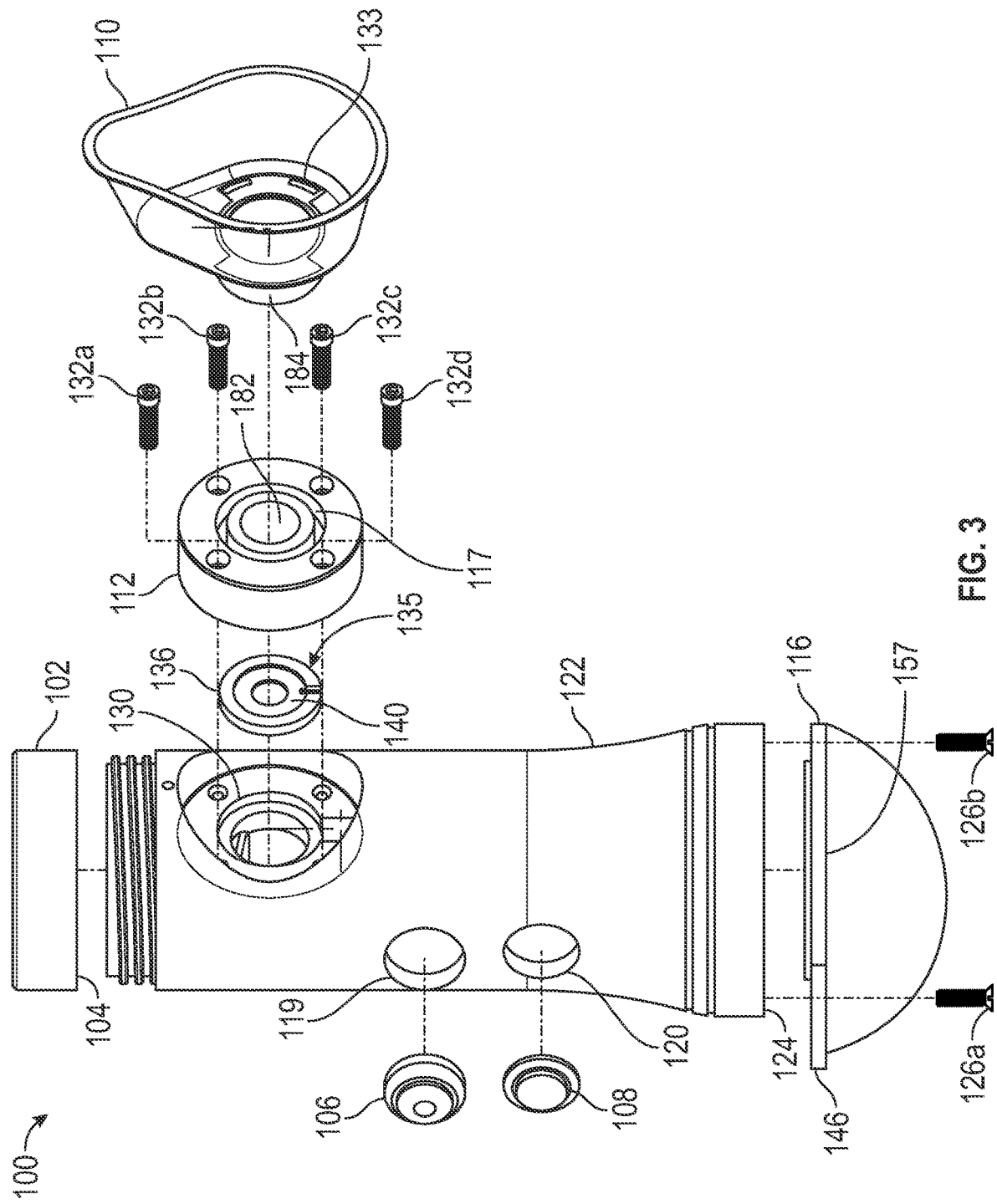
FIG. 3 is an exploded view of a nebulizer.

FIG. 3 is a cross-sectional front view of the nebulizer, illustrating an attachment of the expansion chamber 182 in a counter-sunk hole into the tubular portion 114 using screws 132a, 132b, 132c, and 132d, according to some embodiments of the present invention.

Figure 2:
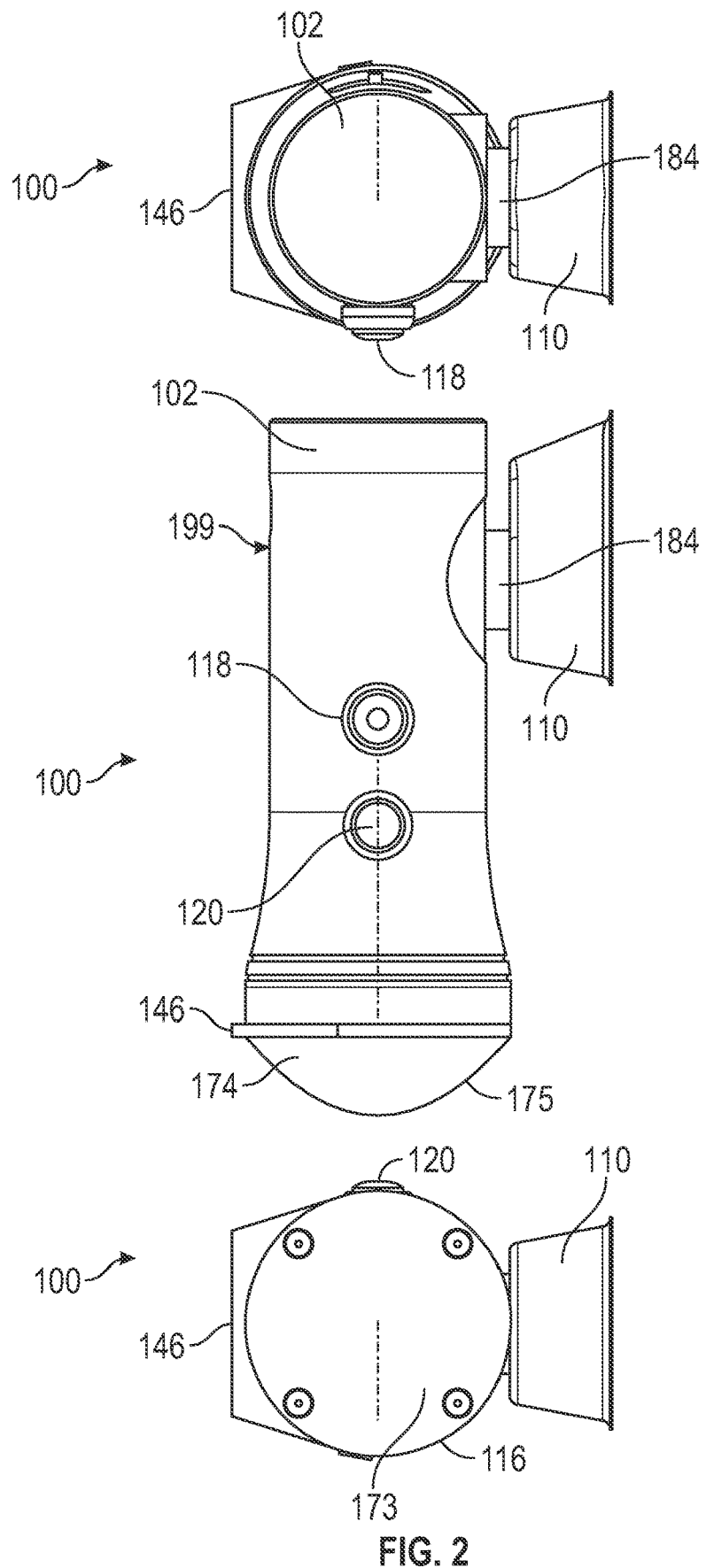
FIG. 2 shows end views of a nebulizer relative to a front view of the nebulizer.

In some embodiments of the present invention, shown in FIGS. 2 and 3, the expansion chamber 182 is surrounded by a cylindrical wall 112 which is removably joined to the housing 199 via screws 132a, 132b, 132c, and 132d. This enables the expansion chamber to be removed for cleaning, and further allows access to the vibration element 135, for maintenance or replacement of the vibration element 135. Thus, one or more first screw holes extend along the cylindrical wall 112 and are aligned with respective second screw holes that extend in the same direction in the housing 199. In this manner, screws 132 can traverse both the first screw openings and the second screw hole, to join the expansion chamber 182 to the housing 199.

When the expansion chamber 182 is joined to the housing 199, a circumferential silicon gasket is pressed by the outer side of the vibration element 135 onto a ring seat of a first counter-sunk socket 130 in tubular portion 114. This creates a hermetic seal which prevents the medicament from flowing from the first reservoir 113 into the expansion chamber 182 while in liquid form.

According to some embodiments of the present invention, the housing 199 includes a first cap 102. The housing 199 has a first open end 104 where there is an entryway to the third reservoir 115 for the liquid, which the first cap 102 covers. The first cap 102 has an internal screw thread 103a. The first open end 104 of the housing 199 has external screw threads 103b at the first open end 104. The internal screw thread 103a of the first cap 102 engages the external screw threads 103b of the entryway to the third reservoir 115 so that the first cap 102 closes the third reservoir 115. When the nebulizer 100 is in a generating position to generate mist from the liquid, the housing 199 is held upright so that the first cap 102 is a 'top' cap at the upper end of the housing 199.

In use to generate mist, the nebulizer 100 is held upright with the first cap 102 and first open end 104 uppermost. When the nebulizer 100 is held upright, the liquid drains down from the third reservoir 115, then into the second reservoir 139, and then into the first reservoir 113.

The second reservoir 139 has a floor 141 made of solid material of the housing 199. The floor 141 slopes from proximate the side of the housing 199 distal from the vibration element 135 to the first drain passage 161 into the first reservoir 113 adjacent the vibration element 135. The floor 141 is closest to third reservoir 115 where the floor 141 is proximate the side of the housing 199 distal from the vibration element 135. So when the housing 199 is held upright in the mist generating position of the nebulizer 100, the floor 141 slopes downward toward the first drain passage 161 and the liquid drains down from the second reservoir 139 through the first drain passage 161 into the first reservoir 113.

The first cap 102 is removable from the tubular portion 114 of the housing 199 and allows access to the third reservoir 115 so that the second reservoir 139 and first reservoir 113 can be filled. In this manner, the reservoirs may be cleaned, a medicament may be inserted in the reservoirs, or a medicament may be poured out of the reservoirs. In some embodiments of the present invention, the first cap 102 is a threaded cap with internal screw threads 103a, which cooperate with external screw threads 103b of the housing 199. In some embodiments of the present invention, the first cap 102 includes one or more vent holes (not shown), configured for maintaining atmospheric pressure in the first reservoir 113 even as the medicament is being pumped out of the reservoir and directed to the nose inhalation device 110.

The housing 199 includes a bottom closure plate the closure cap 157, as shown in FIG. 3. The closure cap 157 is removable from the tubular portion 114 of the housing 199, as shown in FIGS. 1 to 3, which allows access to an electronics bay 155.

The electronics bay 155 is accessible through a second entryway 118 of the tapered section 122 of the housing 199. The second entryway 118 has a tubular or cylindrical rim 124 of the housing 199 which is at the opposite end of the housing 199 from the first open end 104 closed by the first cap 102.

To put the nebulizer 100 into use, the housing 199 is held upright with first cap 102 uppermost and the bottom closure cap 157 lowermost. The bottom closure cap 157 comprises an attached or attachable portion 174, which has a portion of an egg-shaped rim 175 or portion of a sphere-shaped rim. The closure cap 157 and the egg or spherical shaped portion 174 are attached to the cylindrical rim 124, the second entryway 118, by screws 126a, 126b. The screws are received in screw holes in the cylindrical rim 124 of the tubular portion 114 opposite where the first cap 102 connects.

So the housing 199 will roll on the egg-shaped rim 175 if the egg-shaped rim 175 is placed on a substantially horizontal surface with the housing 199 longitudinally upright. Examples of such a substantially horizontal surface include a counter top, or a sink top, or a table top. The housing 199 will roll on the egg-shaped rim 175 until the nebulizer 100 rests with the housing 199 prone on the substantially horizontal surface.

When the nebulizer 100 is in a storage position, the housing 199 is substantially horizontal, as the housing 199 would be when the housing 199 rests prone on the substantially horizontal surface.

The closure cap 157 of the housing 199 comprises an anti-roll edge 146. The anti-roll edge 146 is on an opposite side of the axis of rolling of the tubular portion 114 as the expansion chamber 182. The anti-roll edge 146 is linear and configured to stabilize the nebulizer 100 in the stable position against rolling when the tubular portion 114 lays prone on a flat surface. In the stable position the anti-roll edge 146 faces down on the flat surface.

The expansion chamber 182 has an exit from the housing 199 which faces upwards because the expansion chamber 182 is on the opposite side of the axis of rolling as the anti-roll edge. In the stable position, the first reservoir 113 is beneath the porous mesh 140. So putting the anti-roll edge 146 down on the surface so that the nebulizer 100 rests prone in the stable position arranges the first reservoir 113 to be underneath the porous mesh 140. Liquid in the first reservoir 113 drains down from first reservoir 113 into the second reservoir 139 and, therefore, does not seep through the porous mesh 140 when the nebulizer 100 is in the stable position.

The closure cap 157 of the housing 199 comprises a circular or oblong edge 116, which is chamfered by the anti-roll edge 146. The circular or oblong edge 116 is located axially aligned with the exit in the housing 199 of the expansion chamber 182. The circular or oblong edge 116 is adjacent and substantially matching with the cylindrical rim 124 of the second entryway 118 of the housing 199. The center of mass of the housing 199 is intermediate the central axis of the tubular portion 114 of the housing 199 and the anti-roll edge 146. Consequently, the center of mass applies a moment to the housing 199 when the housing 199 is prone on a surface that urges the housing 199 to roll so that anti-roll edge 146 faces the surface. That is, the housing 199 is urged to roll toward the storage position. The housing 199 is thereby automatically rolled to the storage position or adjacent to it. The first reservoir 113 is thereby put below the porous mesh 140. The second reservoir 139 is put under the first reservoir 113, and so the liquid drains out of the first reservoir 113 and into the second reservoir 139, rather than seeping through the porous mesh 140 into the expansion chamber 182.

The nose inhalation device 110 is concave, so as to encompass the user's nose. The nose inhalation device 110 has a front open side configured to be placed on the user's face and a back side. The back side has an inlet defined by expansion tube 184 configured to receive the mist from the expansion chamber 182.

In a variant, the nose inhalation device 110 also includes a rotatable perforated loop, located behind the flat portion, touching the flat portion, and surrounding the expansion tube 184. The rotatable perforated loop has perforations aligned with the air holes 133. The rotatable perforated loop can be rotated about the expansion tube 184 to misalign the perforations and the air holes. In this manner the air holes can be completely covered or partially covered, to adjust the amount of air that enters the nose inhalation device 110 from the rear end thereof, and to control the mix ratio between outside free air and medicament in the nose inhalation device 110.

The electronics bay 155 may have a connection to a sensor, such as a fingertip pulse oximeter. The readings of the oximeter indicate blood oxygen level and pulse of the patient. If the blood oxygen level is too low, the rotatable perforated loop can be rotated by the user or medical personnel to partially or fully align with the air holes 133 to allow more air from outside to reach the user.

In some embodiments of the present invention, the nebulizer 100 includes a micro-motor configured to rotate the perforated loop, to open or close the air holes 133. In a variant, the operation of the micro-motor is controlled by a processing unit 194 (described below) according to one or more parameters. The parameters may include parameters measured by sensors associated with the nebulizer 100. For example, if an oximeter senses that the patient's blood oxygen level is below a certain threshold (e.g., 98%), the data is relayed to a processing unit 194. The processing unit 194 then controls the micro-motor to rotate the perforated loop in order to open the air holes 133 and cause more fresh air to enter the nose inhalation device 110.

In some embodiments of the present invention, the vibration element 135 is in the form of an ultrasonic piezoelectric nanoparticle transducer as is the piezo actuator 136. The transducer is flat and may be in the shape of a disc and be washer shaped. The transducer has a solid outer ridge surrounding a porous mesh 140. The porous mesh 140 has perforations or pores of a desired size, which allow the passage of the droplets of the desired size therethrough, from the first reservoir 113 to the expansion chamber 182. A first counter-sunk socket 130 is indented into the exterior tubular portion 114 of the housing 199 proximate the first open end 104 and level to the first reservoir 113. So the first counter-sunk socket 130 is the same axial distance from the first open end 104 as from the first reservoir 113. The outer diameter of the washer shaped piezo actuator 136 just fits in the first counter-sunk socket 130. The cylindrical wall 112 of the expansion chamber 182 just fits into a second larger diameter counter-sunk hole which is concentric with the first counter-sunk socket 130. The vibration element 135 is disposed between the first reservoir 113 and the expansion chamber 182. The piezo actuator 136 is compressed firmly between the expansion chamber 182 and base of the first counter-sunk socket 130. The vibration element 135 is thus held firmly in place so that the porous mesh 140 separates the space in the interior of the expansion chamber 182 from the first reservoir 113. In some embodiments the transducer may be wire wound or ceramic.

In some embodiments of the present invention, the perforations or pores in the porous mesh 140 have diameter of 12 μm. The vibration frequency of the transducer may be, for example, 108 kHz. This causes the liquid medicament to be transformed into a mist of 11 μm droplets and drives the mist toward the nose inhalation device 110. A non-limiting example of a transducer that can be used in the present invention is a 16 mm 5 volt nanoparticle ceramic transducer vibrating at 108 kHz. The transducer comprises a silicon surround seal. In some embodiments of the present invention, the operation of the transducer is micro-pulsed (stopped and restarted several times), in order to prevent the transducer from nebulizing the medicament too quickly, and to ensure that the proper amount of medicaments mist is delivered to the patient's nose. The micro-pulsing of the transducer is optionally controlled by the processing unit 194. In some tests run by the inventor, the right flow of nebulized medicament was achieved by starting and stopping the operation of the transducer 200,000 to 400,000 times per minute, in order to nebulize 0.20 ml of insulin over a time of 1.5 to 4.5 minutes—which is the time in which the 0.20 ml of insulin can be absorbed by the olfactory and trigeminal nerves and transferred to the brain. One test was for two minutes each two times a day, once in the morning and once in the evening.

The electronics bay 155 is a cavity in the tubular portion 114. There is an on/off button 108 set at a first socket 120 in the outer wall of the tubular portion 114. The first socket 120 is located proximate the electronics bay 155. The on/off button 108 is configured to be manipulated by a user to allow or deny flow of electrical power to the vibration element 135, thereby turning the nebulizer 100 on and off. In a variant, the electronic bay also includes a battery 131 to power the vibration element 135. The battery 131 may be removable and replaceable. The battery 131 may be rechargeable.

In a variant, the electronics bay 155 includes a timer to time the operation of the nebulizer 100 and turn off the vibration element 135 after a certain time period has passed. In a variant, the tubular portion 114 includes a pause button 106, allowing the user to pause the operation of the nebulizer 100 without resetting the timer. When the pause button 106 is selected a second time, the nebulizer 100 operates again, and the timer continues counting from the time at which it was paused. The pause button 106 is set at a second socket 119 in the outer wall of the tubular portion 114. The second socket 119 is located proximate the electronics bay 155 and proximate the first socket 120.

In some embodiments of the present invention, the electronics bay 155 includes a processing unit 194, a nonvolatile memory unit, and a communication unit. The processing unit 194 is configured for processing data, the memory unit is configured for storing data. The communication unit is configured for transferring data to and from an external unit. For example, the data may be indicative of a treatment regime for a patient and includes instructions for the operation of the nebulizer 100 according to the treatment regime. When the patient turns the nebulizer 100 on, the nebulizer 100 operates for a certain amount of time dictated by the treatment regime. This data about the user may be transferred to the memory unit via the communication unit.

In a variant, the nebulizer 100 includes a medicament quantity indicator. The indicator includes a measuring device located in the reservoir. The quantity indicator includes an output unit (screen, speaker, lamp, haptic unit) on the exterior of the housing 199 configured to inform the user that the quantity of medicament in the reservoir is too low and the reservoir needs to be refilled.

The primary purpose of the present invention is to service intranasal insulin therapy. The present invention does this by delivering a reliable, specific sized droplet for medicament uptake by the body. Droplets between 1-9 microns service medicine for lung, droplet sizes of 10-20 microns service the upper regions of sinus cavity and attached trigeminal and olfactory nerve and pass the blood brain barrier, over 20 microns goes to and through the throat and is swallowed. The nasal nebulizer 100 of the present invention targets a range of 10-17 microns for droplet size.

The invention has been described by way of examples to illustrate principles. Since numerous modifications and changes will readily occur to those skilled in the art, it is not desired to limit the invention to the exact construction and operation shown and described, and accordingly, all suitable modifications and equivalents may be resorted to, falling within the scope of the claims.

The invention claimed is:
1. A nebulizer for nebulizing a liquid into a mist, comprising the following:
a first reservoir and a second reservoir having a first drain passage for the liquid to said first reservoir,
an expansion chamber having a first side adjacent to said first reservoir and an exit to the exterior of said nebulizer, the expansion chamber being configured to channel the mist nebulized from the liquid out of the nebulizer through the exit,
a vibration element disposed between said opening of said expansion chamber and said first reservoir, and the vibration element having a porous mesh through which the liquid in said first reservoir is nebulized into the mist on activation of the vibration element, and
the nebulizer having a shape and weight distribution to rest in a stable storage position and roll toward said stable storage position from any other position, wherein said liquid drains from said first reservoir through said first drain passage to said second reservoir in said stable storage position.

2. The nebulizer according to claim 1 where the second reservoir is disposed to drain the liquid into the first reservoir to contact the mesh when the nebulizer is in a mist generating position.

3. The nebulizer according to claim 1 comprising a third reservoir having a second drain passage for said liquid to the second reservoir, and in the stable storage position the liquid drains from the second reservoir through the second drain passage to the third reservoir.

4. The nebulizer according to claim 1 wherein the volume of the second reservoir exceeds the volume of the first reservoir.

5. The nebulizer according to claim 1 wherein the nebulizer has an axis of rolling, around which the expansion chamber, vibration element, first reservoir, passage, and second reservoir rotate when the nebulizer rolls.

6. The nebulizer according to claim 1 wherein the mesh lies in a first plane of the vibration element, wherein a center of mass of the nebulizer is located on a line which passes through the second reservoir and is parallel to the first plane wherein the expansion chamber, vibration element, and first reservoir are located on a same side of the axis of rolling.

7. The nebulizer according to claim 1 wherein the mesh lies in a first plane of the vibration element, wherein a center of mass of the nebulizer is located on a line which passes through the second reservoir and is parallel to the first plane wherein the nebulizer comprises an edge on an opposite side of the axis of rolling as the expansion chamber, the edge configured to stabilize the nebulizer in the stable position against rolling.

8. The nebulizer according to claim 1 wherein the shape of the nebulizer is configured to roll on a flat surface.

9. The nebulizer according to claim 1 wherein the storage position is in a stable position against rolling wherein the first and second reservoirs, the first drain passage, the expansion chamber, and the vibration element are disposed proximate where the nebulizer is openable and closable to put liquid.

10. The nebulizer according to claim 1 comprising a convex base on a longitudinal end of the nebulizer distal from the second reservoir.

11. The nebulizer according to claim 1 comprising a nose inhalation device having an inlet joined to the exit of the expansion chamber and configured to receive the mist from the expansion chamber.

12. The nebulizer according to claim 11 wherein the nose inhalation device has a curved lip which provides an unstable rest on a rolling surface which urges the nebulizer to roll toward a storage position when resting on the lip of the nose inhalation device and the housing.

13. The nebulizer according to claim 1 having a tubular housing configured to house the first reservoir, the second reservoir, the first drain passage, and the vibrating element.

14. The nebulizer according to claim 13 wherein the center of mass of the tubular housing is offset from the axis of the tubular housing to urge the nebulizer to roll to the stable storage position.

15. The nebulizer according to claim 13 wherein the housing has a first opening to put the liquid into the second reservoir and allow the liquid out of the second reservoir.

16. The nebulizer according to claim 13 wherein the exit is through an external wall of the housing.

17. The nebulizer according to claim 16 wherein the exit faces upward with the nebulizer in the storage position.

18. The nebulizer according to claim 16 wherein the vibration element is intermediate the exit and the first reservoir.

19. A method of repositioning a nebulizer as disclosed in claim 1 to the storage position from a position where the second reservoir is disposed to drain the liquid into the first reservoir to contact the mesh, including laying the nebulizer on a flat surface and allowing the nebulizer to roll toward the stable position.

20. The method of repositioning a nebulizer according to claim 19, wherein the nebulizer has an axis of rolling, around which the expansion chamber, vibration element, first reservoir, passage, and second reservoir rotate when the housing rolls, and the nebulizer comprises an edge on an opposite side of the axis of rolling as the expansion chamber, the edge configured to stabilize the nebulizer in the stable position against rolling, the method including laying the edge on the flat surface to set the nebulizer in the stable position.

* * * * *